US010391151B2

(12) United States Patent
Perlman

(10) Patent No.: US 10,391,151 B2
(45) Date of Patent: Aug. 27, 2019

(54) DILUTE SURFACTANT OR ISOLATED SURFACTANT PROTEIN SOLUTION FOR THE REDUCTION OF SURFACE TENSION IN THE LUNG

(71) Applicant: The Trustees of the Stevens Institute of Technology, Hoboken, NJ (US)

(72) Inventor: Carrie E. Perlman, New York, NY (US)

(73) Assignee: The Trustees of the Stevens Institute of Technology, Hoboken, NJ (US)

(*) Notice: Subject to any disclaimer, the term of this patent is extended or adjusted under 35 U.S.C. 154(b) by 125 days.

(21) Appl. No.: 15/194,096

(22) Filed: Jun. 27, 2016

(65) Prior Publication Data

US 2016/0375106 A1 Dec. 29, 2016

Related U.S. Application Data

(60) Provisional application No. 62/185,967, filed on Jun. 29, 2015.

(51) Int. Cl.
*A61K 38/17* (2006.01)
*A61K 9/00* (2006.01)
*A61K 9/08* (2006.01)

(52) U.S. Cl.
CPC .......... *A61K 38/395* (2013.01); *A61K 9/0082* (2013.01); *A61K 9/08* (2013.01)

(58) Field of Classification Search
CPC ....... A61K 38/00; A61K 9/0082; A23L 33/18; C07K 14/785
See application file for complete search history.

(56) References Cited

U.S. PATENT DOCUMENTS

| 4,216,776 | A | 8/1980 | Downie |
| 6,180,142 | B1 | 1/2001 | Taeusch |
| 8,967,144 | B2 | 3/2015 | Lurie |
| 9,504,796 | B2 | 11/2016 | Perlman |
| 2009/0208581 | A1 | 8/2009 | Edwards et al. |
| 2015/0125515 | A1 | 5/2015 | Notter et al. |
| 2016/0067210 | A1 | 3/2016 | Perlman |
| 2017/0021126 | A1 | 1/2017 | Perlman |

FOREIGN PATENT DOCUMENTS

WO WO2013120058 A2 * 8/2013 ............. A61K 38/47

OTHER PUBLICATIONS

Terry, M. et al., Pulmonary Distribution of Lucinactant and Poractant Alfa and Their Peridosing Hemodynamic Effects in a Preterm Lamb Model of Respiratory Distress Syndrome, Pediatric Research, vol. 68, No. 3, (2010), 193-198.
Tierney, D. et al., Altered surface tension of lung extracts and lung mechanics, J Appl Physiol, 20: 1253-1260, 1965.
Tsuchida et al., "Atelectasis Causes Alveolar Injury in Nonatelectatic Lung Regions", American Journal of Respiratory Critical Care Medicine, vol. 174, (2006), pp. 279-289.
Tsuda, S. et al., DNA damage induced by red food dyes orally administered to pregnant and male mice, Toxicol Sci, 61:92-99, 2001.
Ueda, T. et al., Distribution of surfactant and ventiliation in surfactant-treated preterm lambs, Journal of Applied Physiology, vol. 76, No. 1, (1994), 45-55.
Varisco, B. M. (2011 ). The pharmacology of acute lung injury in sepsis. Advances in pharmacological sciences, 2011.
Veldhuizen, R. et al., Pulmonary surfactant subfractions in patients with the acute respiratory distress syndrome, Am J Respir Crit Care Med, 152: 1867-1871, 1995.
Von Nahm En, A. et al., The phase behavior of lipid monolayers containing pulmonary surfactant protein C studied by fluorescence light microscopy, Eur Biophys, J, 26, (1997), 359-369.
Voss, T. et al., Primary structure differences of human and surfactant-associated proteins isolated from normal and proteinosis lung, Biochimica et Biophysica Acts, 1138, (1992), 261-267.
Walther, F. et al., A Synthetic Segment of Surfactant Protein A: Structure, in Vitro Surface Activity, and in Vivo Efficacy, Pediatric Research, 39(6), (1996), 938-946.
Walther, F. et al., Hydrophobic Surfactant Proteins and Their Analogues, Neonatology, 91, (2007), 303-310.
Walther, F. et al., Surfactant protein C peptides with salt-bridges ("ion-locks") promote high surfactant activities by mimicking the a-helix and membrane topography of the native protein, PeerJ 2:e485; DOI 10.7717/peerj.485, published Jul. 15, 2014.
Wang, Z. et al., Acylation of Pulmonary Surfactant Protein-C Is Required for Its Optimal Surface Active Interactions with Phospholipids, The Journal ofBiological Chemistry, vol. 271, No. 32, (1996), 19104-19109.

(Continued)

*Primary Examiner* — Marcela M Cordero Garcia
*Assistant Examiner* — Jia-Hai Lee
(74) *Attorney, Agent, or Firm* — Greenberg Traurig, LLP

(57) ABSTRACT

In permeability lung edema, cardiogenic lung edema or neonatal respiratory distress, there is heterogeneous liquid distribution throughout the lungs. The excess alveolar liquid reduces gas exchange. Mechanical ventilation is used to improve gas exchange. In the presence of heterogeneous liquid distribution, there are surface tension-dependent stress concentrations in septa separating aerated from flooded alveoli. Mechanical ventilation, by inflating the lung above normal volumes, thus increasing surface tension above normal, exacerbates the stress concentrations and consequently injures, or exacerbates pre-existing injury of, the alveolar-capillary barrier. Any means of lowering surface tension should lessen ventilation injury of the lung. In the present invention, dilute exogenous surfactant solution or surfactant protein C solution interacts with albumin to lower surface tension, likely through effective promotion of surfactant lipid adsorption. Dilute surfactant or SP-C solution could be administered via either the trachea or the vasculature. Either solution could be delivered in the absence or presence of albumin or alternative facilitating solute, to lower surface tension and lessen ventilation injury of the heterogeneously flooded lung.

28 Claims, 4 Drawing Sheets

Specification includes a Sequence Listing.

(56) References Cited

OTHER PUBLICATIONS

Ware, L. et al., The acute respiratory distress syndrome, N Engl J Med, 342: 1334-1349, 2000.
Warr, R. et al., Low molecular weight human pulmonary surfactant protein (SP5): Isolation, characterization, and cDNA and amino acid sequences, Proc Natl Acad Sci USA, vol. 84, (1987), 7915-7919.
Warriner, H. et al., A concentration-dependent mechanism by which serum albumin inactivates replacement lung surfactants, Biophys J, 82: 835-842, 2002.
Weg, J. et al., Safety and potential efficacy of an aerosolized surfactant in human sepsis-induced adult respiratory distress syndrome, JAMA, 272: 1433-1438, 1994.
Whitsett, J. et al., Hydrophobic Surfactant-Associated Protein in Whole Lung Surfactant and Its Importance for Biophysical Activity in Lung Surfactant Extracts Used for Replacement Therapy, Pediatric Research, vol. 20, No. 5, (1986), 460-467.
Wilkins et al., "Egan's Fundamentals of Respiratory Care", Mosby, Inc. (2009), pp. 939-941.
Willson, D. et al., Effect of exogenous surfactant (calfactant) in pediatric acute lung injry: a randomized controlled trial, JAMA, 293: 470-476, 2005.
Willson, D. et al., Surfactant for Pediatric Acute Lung Injury, Pediatr Clin N Am, 55, (2008), 545-575.
Wu, Y. et al., Lung ventilation injures areas with discrete alveolar flooding, in a surface tension-dependent fashion, J Appl Physiol, 117: 788-796, 2014.
Yapicioglu, H. et al., The use of surfactant in children with acute respiratory distress syndrome: efficacy in terms of oxygenation, ventilation and mortality, Pulmonary Pharmacology & Therapeutics, 16, (2003), 327-333.
Yu, S. et al., Effect of pulmonary surfactant protein A and neutral lipid on accretion and organization of dipalmitoylphosphatidycholine in surface films, Journal of Lipid Research, vol. 37, (1996), 1278-1288.
Yu, S. et al., Reconstitution of surfactant activity by using the 6 kDa apoprotein associated with pulmonary surfactant, Biochem J, 236, (1986), 85-89.
Yu, S. et al., Role of bovine pulmonary surfactant-associated proteins in the surface-active property of phospholipid mixtures, Biochim Biophys Acta, 1046: 233-241, 1990.
Yu. S. et al.. Characterization of the small hydrophobic proteins associated with pulmonary surfactant. Biochimica et Biophysica Acta. vol. 921. No. 3, (1987), 437-448.
Zasadzinski, J. et al., Inhibition of pulmonary surfactant adsorption by serum and the mechanisms of reversal by hydrophilic polymers: theory, Biophys J, 89: 1621-1629, 2005.
Zasadzinski, J. et al., Overcoming rapid inactivation of lung surfactant: Analogies between competitive adsorption and colloid stability, Biochimica et Biophysica Acta, 1798, (2010), 801-828.
Final Office Action dated May 12, 2016 in U.S. Appl. No. 13/650,759.
Krishnan et al., "High-Frequency Ventilation for Acute Lung Injury and ARDS", Chest, vol. 118, No. 3, Sep. 2000, pp. 795-807.
Landmann, E. et al., Protein content and biophysical properties of tracheal aspirates form nennates with respiratory failure, Klin Padiatr, 214, (2002), 1-7.
Lewis, J. et al., Altered Alveolar Surfactant Is an Early Marker of Acute Lung Injury in Septic Adult Sheep, American Journal of Respiratory and Critical Care Medicine, vol. 150, No. 1, (1994), 123-130.
Lewis, J. et al., Lung function and surfactant distribution in saline-lavaged sheep given instilled vs. nebulized surfactant, Journal of Applied Physiology, vol. 74, No. 3, (1993), 1256-1264.
Li, J. et al., The N-terminal Propeptide of Lung Surfactant Protein C is Necessary for Biosynthesis and Prevents Unfolding of a Metastable a-Helix, J Mol Biol, 338, (2004), 857-862.
Liau, D. et al., Functional Abnormalities of Lung Surfactant in Experimental Acute Alveolar Injury in the Dog, Am Rev Respir Dis, 136, (1987), 395-401.
Lukovic, D. et al., Production and characterisation of recombinant forms of human pulmonary surfactant protrain C (SP-C): Structure and surface activity, Biochimica et Biophysica Acta, 1758, (2006), 509-518.
Mazela, J. et al,. Comparison of poractant alfa and lyophilized lucinactant in a preterm lamb model of acute respiratory distress, Pediatric Research, vol. 72, No. 1, (2012), 32-37.
Moison, R. et al., Plasma Proteins in Acute and Chronic Lung Disease of the Newborn, Free Radical Biology & Medicine, vol. 25, No. 3, (1998), 321-328.
Morley, C., Systematic review of prophylactic vs rescue surfactant, Archives of Disease in Childhood, 77, (1997), F70-F74.
Nakamura, H. et al., Monomolecular surface film and tubular myelin figures of the pulmonary surfactant in hamster lung, Cell Tissue Res, 241, (1985), 523-528.
National Center for Biotechnology Information. PubChem Compound Database; CID=65191, https://pubchem.ncbi.nlm.nih.gov/compound/65191 (accessed May 6, 2016).
Nicholas, T. Pulmonary Surfactant: No mere paint on the alveolar wall, Respirology, 1, (1996), 247-257.
Niemarkt, H. et al., Effects of less-invasive surfactant administration on oxygenation, pulmonary surfactant distribution, and lung compliance in spontaneously breathing preterm lamb, Pediatric Research, 76, (2014), 166-170.
Non-Final Office Action dated Dec. 11, 2015 in U.S. Appl. No. 13/650,759.
Notter, R. et al., Biophysical Activity of Synthetic Phospholipids Combined with Purified Lung Surfactant 6000 Dalton Apoprotein, Chemistry and Physics of Lipids, 44, (1987) 1-17.
Otsubo, E. et al., Characterization of the Surface Activity of a Synthetic Surfactant with Albumin, Biol Pharm Bull, 25(12), (2002), 1519-1523.
Perlman et al., "Micromechanics of Alveolar Edema", American Journal of Respiratory Cell Molecular Biology, vol. 44, (2011) pp. 34-39.
Petty, T. et al., Abnormalities in Lung Elastic Properties and Surfactant Function in Adult Respiratory-Distress Syndrome. Chest 75: 571-574, 1979.
Petty, T. et al., Characteristics of Pulmonary Surfactant in Adult Respiratory Distress Syndrome Associated with Trauma and Shock, American Review of Respiratory Disease, 115, (1977), 531-536.
Phua, J. et al., Has mortality from acute respiratory distress syndrome decreased over time?: A systematic review, Am J Respir Crit Care Med, 179: 220-227, 2009.
Pison, U. et al., Surfactant Abnormalities in Patients with Respiratory Failure after Multiple Trauma, Am Rev Respir Dis, 140: 1033-1039, 1989.
Plasencia, I. et al., The N-terminal segment of pulmonary surfactant lipopeptide SP-C hasintrinsic propensity to Interact with and perturb phospholipid bilayers, Biochem J, 377, (2004), 183-193.
Polat, B. et al., An experimental and molecular dynamics investigation into the amphiphilic nature of sulforhodamine B, J Phys Chem B, 115: 1394-1402, 2011.
Product Monograph, Curosurf, Chiesi Farmaceutici, Parma, Italy, Sep. 2009.
Robertson, B. et al., Principles of surfactant replacement, Biochimica et Biophysica Acta, 1408, (1998) 346-361.
Rooney, S., Lung Surfactant, Environmental Health Perspectives, 55, (1984), 205-226.
Rubenfeld, G. et al., Incidence and outcomes of acute lung injury, N Engl J Med, 353: 1685-1693, 2005.
Sarin, V. et al., Biophysical and biological activity of a synthetic 8.7-kDa hydrophobic pulmonary surfactant protein SP-B, Proc Natl Acad Sci USA, 87, (1990), 2633-2637.
Schmidt, R. et al., Alteration of fatty acid profiles in different pulmonary surfactant phospholipids in acute respiratory distress syndrome and severe pneumonia, Am J Respir Crit Care Med, 163: 95-100, 2001.
Scientific Committee on Consumer Products (SCCP). Health and Consumer Protection Directorate-General. European Commission. Opinion on Acid Red 52 (Online). http://ec.europa.eu/health/ph_risk/committees/04_sccp/docs/sccp_o_137.pdf [Jun. 24, 2008].

(56) References Cited

OTHER PUBLICATIONS

Seeger, W. et al., Alteration of surfactant function due to protein leakage: special interaction with fibrin monomer, J Appl Physiol, 58: 326-338, 1985.
Seeger, W. et al., Alveolar surfactant and adult respiratory distress syndrome, Clin Investig, 71, (1993), 177-190.
Seeger, W. et al., Differential sensitivity to fibrinogen inhibition of SP-C- vs. SP-B-based surfactants, Am J Physiol Lung Cell Mal Physiol, 262: L286-L291, 1992.
Seeger, W. et al., Surfactant inhibition by plasma proteins: differential sensitivity of various surfactant preparations, Eur Respir J, 6, (1993), 971-977.
Seehase, M. et al., New Surfactant with SP-B and C Analogs Gives Survival Benefit after Inactivation in Preterm Lambs, PLoS ONE, 7(10), (2012), e47631.
Segerer, H. et al., Rapid Tracheal Infusion of Surfactant versus Bolus Instillation in Rabbits: Effects on Oxygenation, Blood Pressure and Surfactant Distribution, Biol Neonate, 69, (1996), 119-127.
Smart, P. et al., An Evaluation of Some Fluorescent Dyes for Water Tracing, Water Resources Research, vol. 13, No. 1, (1977), 15-33.
Smart, P., A review of the toxicity of twelve fluorescent dyes used for water tracing, NSS Bulletin, 46: 21-33, 1984.
Speer, C. et al., Early versus late surfactant therapy in severe respiratory distress syndrome, Lung, Suppl, (1990), 870-876.
Spragg, R. et al., Effect of recombinant surfactant protein C-based surfactant on the acute respiratory distress syndrome, N Engl J Med, 351: 884-892, 2004.
Spragg, R. et al., Recombinant surfactant protein C-based surfactant for patients with severe direct lung injury, Am J Respir Crit Care Med, 183: 1055-1061, 2011.
Spragg. R. et al., Surfactant Replacement Therapy, Clinics in Chest Medicine, vol. 21, No. 3, (2000), 531-541.
St. Clair, C. et al., The Probability of Neonatal Respiratory Distress Syndrome as a Function ofGestational Age and Lecithin/Sphingomyelin Ratio, American Journal of Perinatology, vol. 25, No. 8, (2008), 473-480.
Staub et al., "Pulmonary edema in dogs, especially the sequence of fluid accumulation in lungs", Journal of Applied Physiology, vol. 22, No. 2, (1967), pp. 227-240.
Stawicki et al., "High-Frequency Oscillatory Ventilation (HFOV) and Airway Pressure Release Ventilation (APRV): A Practical Guide", Journal of Intensive Care Medicine, vol. 24, No. 4, Jul./Aug. 2009, pp. 215-229.
Szyperski, T. et al., Pulmonary surfactant-associated polypeptide Cina mixed organic solvent transforms from a monomeric a-helical state into insoluble P-sheet aggregates, Protein Science, 7, (1998), 2533-2540.
Taeusch, H. et al., Inactivation of pulmonary surfactant due to serum-inhibited adsorption and reversal by hydrophilic polymers: Experimental, Biophys J, 89: 1769-1779, 2005.
Takahashi, A. et al., Structure-function relationships of bovine pulmonary surfactant proteins: SP-Band SP-C, Biochim Biophys Acta, 1044: 43-49, 1990.
Tanaka, Y. et al., Lung Surfactants. II. Effects of fatty acids, triacylglycerols and protein on the activity of lung surfactant, Chemical and Pharmaceutical Bulletin, vol. 31, No. 11, (1983), 4100-4109.
Amizuka, T. et al., Surfactant therapy in neonates with respiratory failure due to haemorrhagic pulmonary oedema, Eur J Pediatr, 162, (2003), 697-702.
Anzueto, A. et al., Aerosolized Surfactant in Adults with Sepsis-Induced Acute Respiratory Distress Syndrome. New Engl J Med 334: 1417-1422, 1996.
Bachofen et al., "Experimental Hydrostatic Pulmonary Edema in Rabbit Lungs", The American Review of Respiratory Disease, vol. 147, (1993), pp. 989-996.
Banerjee, R. et al., Ultrastructure of exogenous surfactants using cryogenic scanning electron microscopy, J Biomater Appl, 15, (2001 ), 230-240.

Batenburg, J. et al., The lipids of pulmonary surfactant: dynamics and interactions with proteins. Prag Lipid Res 37: 235-276, 1998.
Baumgart, F. et al., Palmitoylation of Pulmonary Surfactant Protein SP-C is Critical for Its Functional Cooperation with SP-B to Sustain Compression/Expansion Dynamics in Cholesterol-Containing Surfactant Films, Biophysical Journal, 99, (2010), 3234-3243.
Bernhard, W. et al., Commercial versus Native Surfactants: Surface Activity, Molecular Components, and the Effect of Calcium, Am J Respir Crit Care Med, 162, (2000) 1524-1533.
Berry, D. et al., Respiratory distress and surfactant inhibition following vagotomy in rabbits, J Appl Physiol, 61, (1986), 1741-1748.
Bradbury, J., Could treatment of neonatal RDS improve further?, The Lancet, 360, (2002), p. 394.
Braun, A. et al., A Freeze-Fracture Transmission Electron Microscopy and Small Angle X-Ray Diffraction Study of the Effects of Albumin, Serum and Polymers on Clinical Lung Surfactant Microstructure, Biophysical Journal, 93, (2007) 123-139.
Brower et al., "Another "Negative" Trial of Surfactant, Time to Bury this Idea?", American Journal of Respiratory and Critical Care Medicine, vol. 183, (2011 ), pp. 966-968.
Brower. R.G. et al., The Acute Respiratory Distress Syndrome Network. Ventilation with lower tidal volumes as compared with traditional tidal volumes for acute lung injury and the acute respiratory distress syndrome. N Engl J Med 342: 1301-1308,2000.
Cairo et al., "Mosby's Respiratory Care Equipment (Eighth Edition)", 2011, pp. 217-228; 233-238; 377; 398-403 and 685.
Cassidy, K. et al., Liquid Plug Flow in Straight and Bifurcating Tubes, Journal of Biomechanical Engineering, 123, (2001 ), 580-589.
Clements, J., Lung Surfactant: A Personal Perspective, Annu Rev Physiol, 59, (1997) 1-21.
Curstedt, T. et al., Different Effects of Surfactant Proteins Band C—Implications for Development of Synthetic Surfactants, Neonatology, 97, (2010), 367-372.
De Prost, N. et al., Ventilator-induced lung injury: historical perspectives and clinical implications, Annals of Intensive Care, 1 :28, (2011 ), 1-15.
Dhar, P. et al., Liquid Protein Interactions Alter Line Tensions and Domain Size Distributions in Lung Surfactant Monolayers, Biophysical Journal, 102, (2012), 56-65.
Diemel, R. et al., In vitro and in vivo intrapulmonary distribution offtuorescently labeled surfactant, Crit Care Med, vol. 30, No. 5, (2002), 1083-1090.
Dijk, P. et al., A Comparison of the Hemodynamic and Respiratory Effects of Surfactant Instillation during Interrupted Ventilatio nversus Non interrupted Ventilation in Rabbits with Severe Respiratory Failure, Pediatric Research, 45(2), (1999), 235-241.
Ding, J. et al., Effects of Lung Surfactant Proteins, SP-Band SP-C, and Palmitic Acid onMonolayer Stability, Biophysical Journal, 80, (2001 ), 2262-2272.
Dluhy, R. et al., Deacylated Pulmonary Surfactant Protein SP-C Transforms From a-Helical to Amyloid Fibril Structure via a pH-Dependent Mechanism: An Infrared Structural Investigation, Biophysical Journal, 85, (2003), 2417-2429.
Dreyfuss, D. et al., Ventilator-induced lung injury: lessons from experimental studies. Am J Respir Crit Care Med 157: 294-323, 1998.
Goss, C. et al., Incidence of acute lung injury in the United States, Crit Care Med, vol. 31, No. 6, (2003), 1607-1611.
Greenough, A. Expanded use of surfactant replacement therapy, Eur J Pediatr, 159, (2000), 635-640.
Gregory, T. et al., Bovine surfactant therapy for patients with acute respiratory distress syndrome, Am J Respir Crit Care Med, 155, (1997), 1309-1315.
Gregory, T. et al., Surfactant chemical composition and biophysical activity in acute respiratory distress syndrome. J Clin Invest, 88, (1991), 1976-1981.
Gu, J., et al., Pathology and pathogenesis of severe acute respiratory syndrome. The American journal of pathology, 170(4), (2007), 1136-1147.

(56) References Cited

OTHER PUBLICATIONS

Gunther, A. et al., Surfactant alterations in severe pneumonia, acute respiratory distress syndrome, and cardiogenic lung edema. Am J Respir Crit Care Med 153: 176-184, 1996.

Gustafsson, M. et al., Amyloid fibril formation by pulmonary surfactant protein C, FEBS Letters, 464, (1999), 138-142.

Gustafsson, M. et al., Palmitoylation of a pulmonary surfactant protein C analogue affects the surface associated lipid reservoir and film stability, Biochimica et Biophysica Acta, 1466 (2000) 169-178.

Gustafsson, M. et al., The Palmitoyl Groups of Lung Surfactant Protein C Reduce Unfolding into a Fibrillogenic Intermediate, J Mol Biol, 310, (2001), 937-950.

Hall, S. et al., Changes in Subphase Aggregates in Rabbits Injured by Free Fatty Acid, Am J Respir Crit Care Med, 149, (1994) 1099-1106.

Halliday, H., Surfactants: past, present and future. J Perinatol 28, Suppl 1: S47-S56, 2008.

Hallman, M. et al., Evidence of lung surfactant abnormality in respiratory failure. Study of bronchoalveolar lavage phospholipids, surface activity, phospholipase activity, and plasma myoinositol, J Clin Invest, 70: 673-683, 1982.

Heldt. G. et al.. Distribution of Surfactant, Lung Compliance, and Aeration of Preterm Rabbit Lungs after Surfactant Therapy and Conventional and High-Frequency Oscillatory Ventilation, Pediatric Research, vol. 31, No. 3, (1992), 270-275.

Henry, M. et al., Ultrasonic Nebulized in Comparison with Instilled Surfactant Treatment of Preterm Lambs, Am J Respir Crit Care Med, 154, (1996), 366-375.

Holm, B. et al., A biophysical mechanism by which plasma proteins inhibit lung surfactant activity, Chem Phys Lipids, 49, (1988) 49-55.

Holm, B. et al., Content of Dipalmitoyl Phosphatidylcholine in Lung Surfactant: Ramifications for Surface Activity, Pediatric Research, 39(5), (1996), 805-811.

Ikegami, M. et al., A Protein That Inhibits Surfactant in Respiratory Distress Syndrome, Biol Neonate, 50, (1986), 121-129.

Jobe, A. et al., Lung protein leaks in ventilated lambs: effects of gestational age, Journal of Applied Physiology, vol. 58, No. 4, (1985), 1246-1251.

Jobe, A. et al., Permeability of premature lamb lungs to protein and the effect of surfactant on that permeability, Journal of Applied Physiology, vol. 55, No. 1, (1983), 169-176.

Johansson, J. et al., Molecular structures and interactions of pulmonary surfactant components, Eur J Biochem 244: 675-693, 1997.

Jordanova, A. et al., Influence of surfactant protein Con the interfacial behavior of phosphatidylethanolamine monolayers, Eur Biophys J, 38, (2009), 369-379.

Kesecioglu, J. et al., Exogenous natural surfactant for treatment of acute lung injury and the acute respiratory distress syndrome, Am J Respir Crit Care Med, 180: 989-994, 2009.

Kharge, A. et al., Sulforhodamine B interacts with albumin to lower surface tension and protect against ventilation Injury of flooded alveoli. J Appl Physiol, 118, (2015), 355-364.

Kharge, A. et al., Surface tension in situ in flooded alveolus unaltered by albumin, J Appl Physiol, 117: 440-451, 2014.

Kitamura, M. et al., Binding of sulforhodamine B to human serum albumin: a spectroscopic study, Dyes Pigments, 99: 588-593,2013.

Kovacs, H. et al., The Effect of Environment on the Stability of an Integral Membrane Helix: Molecular Dynamics Simulations of Surfactant Protein C in Chloroform, Methanol and Water, J Mol Biol, 247, (1995), 808-822.

Krause, M. et al., Alveolar Recruitment Promotes Homogeneous Surfactant Distribution in a Piglet Model of Lung Injury, Pediatric Research, vol. 50, No. 1, (2001 ), 34-43.

* cited by examiner

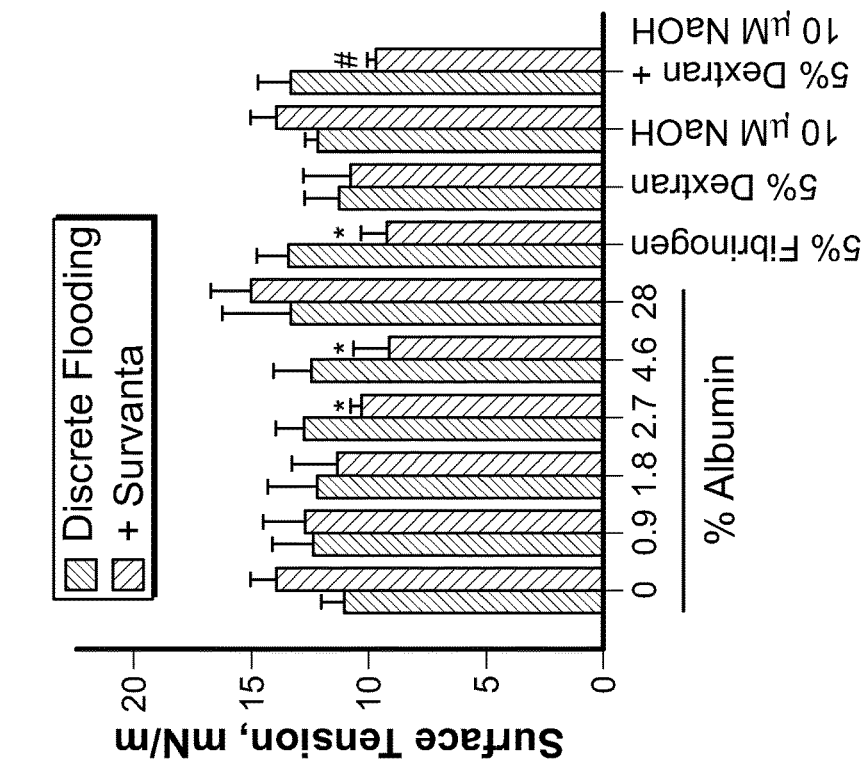
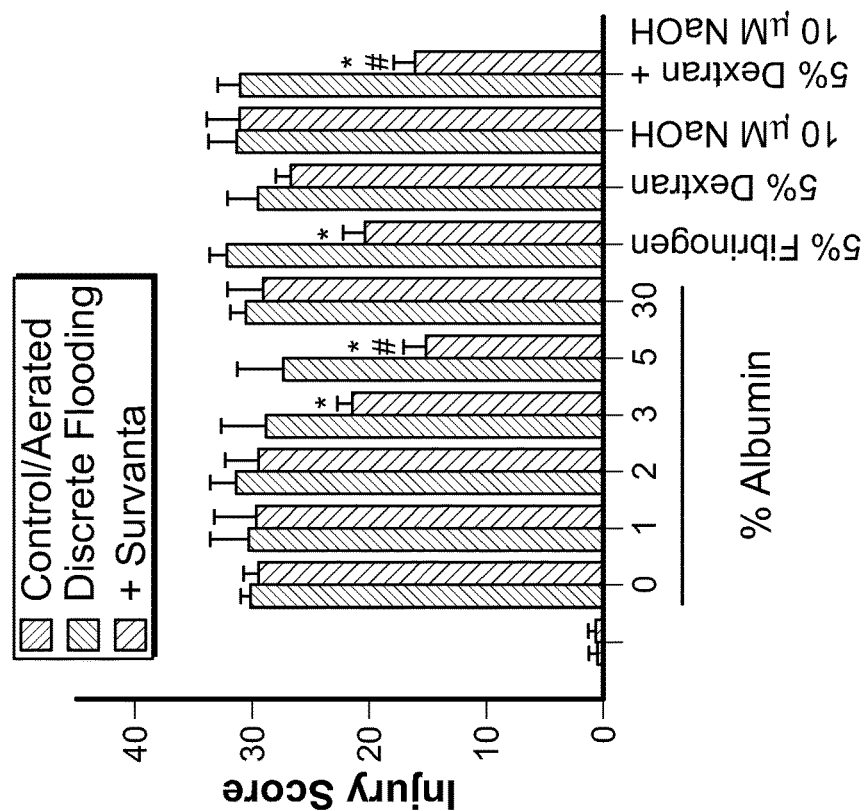
FIG. 1A
FIG. 1B

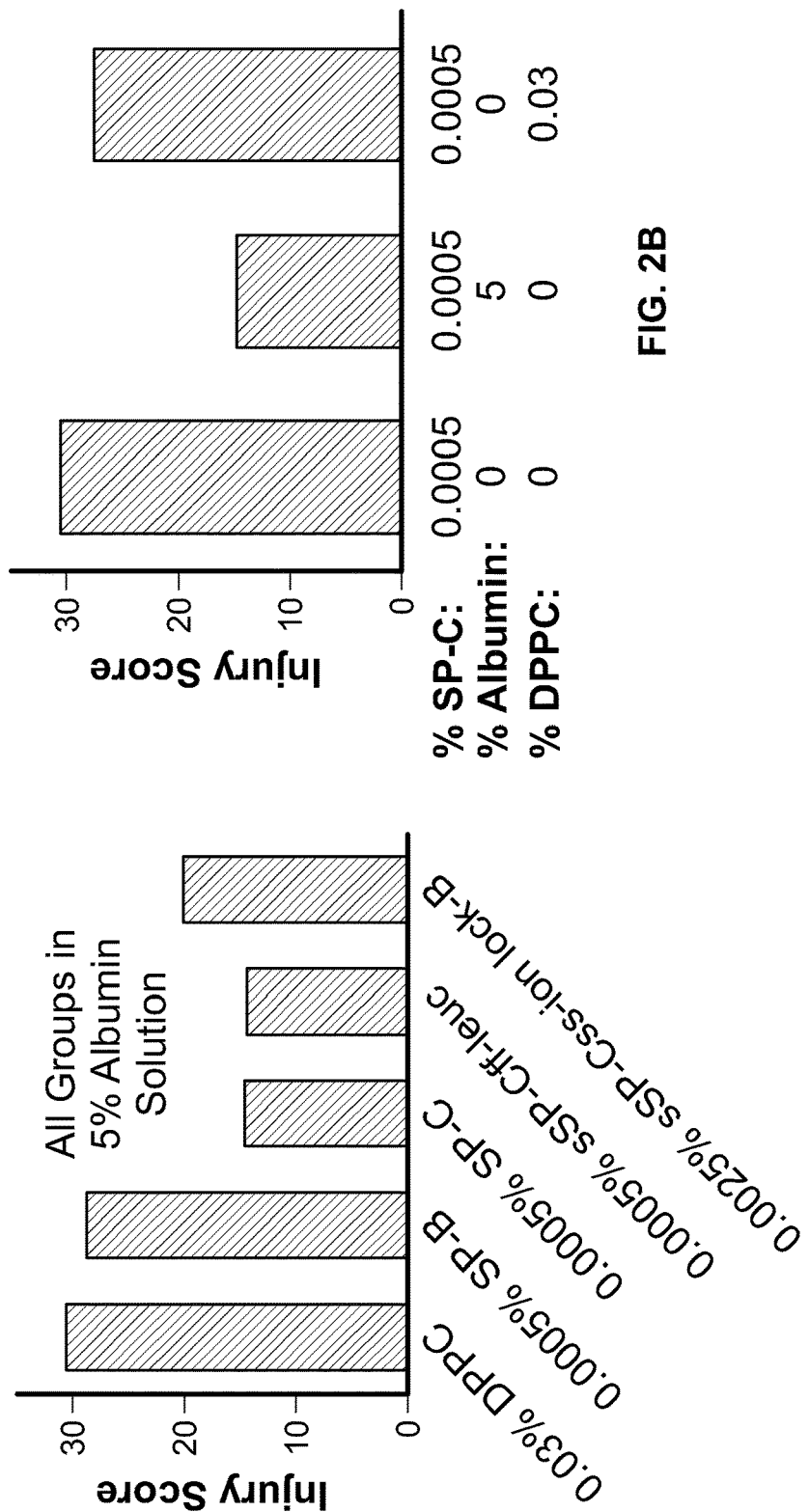

DILUTE SURFACTANT OR ISOLATED SURFACTANT PROTEIN SOLUTION FOR THE REDUCTION OF SURFACE TENSION IN THE LUNG

CROSS-REFERENCE TO RELATED APPLICATIONS

The present application claims the benefit of U.S. Provisional Application No. 62/185,967, filed Jun. 29, 2015, the entire disclosure of which is incorporated by reference herein.

STATEMENT REGARDING FEDERALLY SPONSORED RESEARCH

The present invention was supported in part by funds from the U.S. government (NIH Grant No. RO1 HL113577), and the U.S. Government may therefore have certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is 101995_043101-SeqListing.txt. The text file is 1 KB. It was created on Jun. 20, 2016 and is being submitted via EFS-Web with the filing of the specification.

FIELD OF THE INVENTION

The present invention relates to methods for minimizing mechanical ventilation injury to an edematous lung being subjected to mechanical ventilation. More particularly, the methods of the present invention comprise lowering the surface tension of liquid in alveoli of the edematous lung by providing to the alveoli a surfactant-associated protein and a negatively charged solute.

BACKGROUND OF THE INVENTION

Lung Physiology.

The main passageways for air to travel from the nose or mouth to the lungs are the bronchi, which eventually branch to the bronchioles, which then branch to alveolar ducts. The terminal airspaces of the lungs, the alveoli, where gas exchange takes place, branch off of the alveolar ducts. Air pressure is equal between two adjacent alveoli. Thus, as equal pressures are applied to each side of any wall, or septum, between adjacent air-filled alveoli, such septa are substantially planar in shape. The surface of the alveolus is lined with type I and II alveolar epithelial cells, on top of which there is a thin liquid lining layer. Thus, there is an air-liquid interface in the lungs that has an associated surface tension. Alveolar type II epithelial cells release surfactant, which adsorbs to the interface and maintains low surface tension in the lungs. Lung surfactant is a mixture of phospholipids, the most abundant of which is dipalmitoylphosphatidylcholine (DPPC); neutral lipids; and four surfactant-associated proteins, surfactant protein (SP)-A, SP-B, SP-C and SP-D. Surfactant proteins B and C, which are hydrophobic, facilitate surfactant lipid adsorption. By lowering surface tension, surfactant reduces the pressure required to keep the lungs inflated and reduces the work of breathing.

Inside of alveolar septa are located the pulmonary capillaries. The tissue and liquid between capillary blood and alveolar air constitute the alveolar capillary barrier, across which gas exchange occurs.

Acute Respiratory Distress Syndrome (ARDS) and Ventilation-Induced Lung Injury.

The acute respiratory distress syndrome can be caused by any number of different initial insults. Regardless of cause, with ARDS there is inflammation in the lungs. With inflammation, there is increased permeability of the alveolar-capillary barrier and liquid leaks out of the blood vessels. The liquid carries with it plasma proteins—principally the most abundant plasma protein, albumin, but also plasma proteins present at lower concentrations, such as fibrinogen. When enough liquid escapes from the vessels, liquid begins to enter the alveoli, a condition known as alveolar edema. In flooded alveoli, the air-liquid interface forms a meniscus. Thus, as described by the Laplace relation, flooded alveolar liquid pressure is less than alveolar air pressure, to a degree that is proportional to surface tension at the meniscal interface. The additional liquid in the airspace effectively thickens the alveolar-capillary barrier across which gas exchange occurs.

Further, with alveolar edema, there are regions of the lungs in which alveolar flooding is heterogeneous. That is, aerated and liquid-flooded alveoli are interspersed. 'Intervening' septa, i.e., those located between adjacent aerated and flooded alveoli, are thus subjected to a relatively high air pressure on one side and a relatively low liquid pressure on the other. The air-liquid pressure difference across the intervening septum, which equals the pressure difference across the meniscus of the flooded alveolus and is proportional to surface tension, causes the intervening septum to bow into the flooded alveolus. Thus, at any given lung inflation pressure, the intervening septum is extended beyond its normal length and becomes a site of stress concentration.

Patients with ARDS are treated by mechanical ventilation, which assists gas exchange but often causes an over-distension injury that exacerbates the underlying lung disease and prevents patient recovery. In particular, mechanical ventilation inflates the lung above the volumes reached during spontaneous breathing, thus increasing surface tension above normal and, as a result, exacerbates the surface tension-dependent stress concentrations in intervening septa between aerated and flooded alveoli. Consequently, mechanical ventilation of heterogeneously flooded regions injuriously increases permeability of an initially intact alveolar-capillary barrier to a degree that is proportional to the surface tension of the alveolar liquid in the region.

As over-distension injury is surface tension-dependent, lowering surface tension of the liquid in the alveoli of an edematous lung should directly lessen ventilation injury. Clinical surfactant therapy trials have tested intratracheal instillation of exogenous animal (either bovine, e.g., SURVANTA® (commercially available from Abbvie, Inc. located in North Chicago, Ill., U.S.A.), or porcine) surfactant as a means of lowering surface tension and treating ARDS. SURVANTA® is intended to provide surface-tension lowering properties similar to that of natural (endogenous) lung surfactant and is generally a mixture of bovine-harvested phospholipids, including DPPC, neutral lipids, fatty acids and surfactant proteins B and C; additional DPPC; palmitic acid; and tripalmitin, all suspended in a 0.9% sodium chloride solution. More specifically, SURVANTA® typically has a phospholipid concentration of about 25 milligrams per milliliter (mg/mL), a triglyceride concentration of from about 0.5 mg/mL to about 1.75 mg/mL, and a protein content of less than about 1.0 mg/mL. However, such exogenous surfactant therapy has not reduced ARDS mortality. One possible reason for the failure of exogenous surfactant therapy is heterogeneity of exogenous surfactant distribution throughout the lungs.

Further, the heterogeneous alveolar flooding pattern is attributable to liquid being trapped in discrete alveoli by a 'pressure barrier,' i.e., the presence of a higher liquid pressure at the edge than in the center of flooded alveoli. And the pressure barrier is proportional to surface tension at the air-liquid interface. Lowering surface tension, by lowering the pressure barrier, can facilitate liquid escape from flooded alveoli and redistribution, in a more homogeneous fashion, across neighboring alveoli. Such liquid escape from flooded alveoli reduces alveolar flooding heterogeneity and should reduce the number of stress concentrations present. Thus lowering surface tension should also, by reducing flooding heterogeneity, indirectly reduce mechanical ventilation injury.

Cardiogenic Pulmonary Edema (CPE).

In cardiogenic pulmonary edema, liquid entrance into the alveoli of the lung is driven not by abnormally elevated permeability of the alveolar-capillary barrier but, rather, by abnormally elevated pulmonary capillary blood pressure secondary to left heart dysfunction. As barrier permeability is, at least initially, normal, plasma proteins should be trapped in the no capillaries and plasma protein concentration in the alveolar edema liquid should be low. Yet, quantitative analysis of alveolar liquid in CPE demonstrates that protein concentration is elevated above normal in CPE, to the same degree as in ARDS. Further, in CPE, as in ARDS, there are regions of the lungs in which alveolar flooding is heterogeneous.

It may be that mechanical ventilation of CPE patients exacerbates stress concentrations in regions of heterogeneous alveolar flooding, thus injuring the alveolar-capillary barrier in such regions and leading to plasma protein entrance into the edema liquid. Regardless of the mechanism responsible for the elevated edema liquid plasma protein concentration in CPE patients, however, alveolar flooding pattern and edema liquid plasma protein concentration are similar between CPE and ARDS. In CPE, as in ARDS, lowering surface tension should, by either direct or indirect means, lessen ventilation injury of regions with heterogeneous alveolar flooding.

Neonatal Respiratory Distress Syndrome (NRDS).

Lung surfactant is produced during the third trimester of gestation and is critical to the ability of a baby to breathe unaided. Historically, many premature babies did not survive. Since the 1980's, tracheal instillation of exogenous animal surfactant has been a tremendously successful therapy that has enabled premature babies to live. However, there remains room for improvement in the clinical treatment of NRDS.

As the lungs are entirely filled with liquid prior to the first breath following birth, there are similarities between neonatal and edematous lungs. Neonatal respiratory distress is similar to CPE, in particular, in that both barrier permeability and alveolar liquid protein concentration are, initially, normal/low. However, with mechanical ventilation, barrier permeability and alveolar liquid protein content increase. This increase is likely attributable to mechanical ventilation causing heterogeneous aeration, thus leaving behind heterogeneous flooding and resulting in exacerbation of stress concentrations in heterogeneously flooded regions. An important difference between NRDS and both ARDS and CPE is that in NRDS there is less surfactant present than in mature lungs.

In NRDS, lowering surface tension with exogenous surfactant therapy is already beneficial. However lowering surface tension to a greater degree, or more uniformly throughout the lungs, should further lessen ventilation injury of regions with heterogeneous flooding.

Surface Tension Assessment Methods.

Surface tension is assessed in the isolated lung and in vitro using four complementary methods, as follows.

Method 1. Surface tension determination in the adult rat lung. In the isolated adult rat lung, a surface alveolus is micropunctured and a test solution, labeled with a low concentration of fluorescent dye verified not to alter surface tension, is instilled. In flooded alveoli, the air-liquid interface forms a meniscus, at which surface tension is determined as follows. Alveolar air pressure is determined with a transducer at the trachea of the constantly-inflated lung. Alveolar liquid phase pressure is determined by servo-nulling pressure measurement. Meniscus radius of curvature is determined by confocal microscopy. Surface tension is calculated according to the Lapalce relation.

Method 2. Ventilation 'injury score' in the adult rat lung. In the isolated, perfused adult rat lung, a surface alveolus is micropunctured and a non-fluorescent test solution is instilled. In experimental regions, a sufficiently large volume of liquid is instilled to generate a pattern of heterogeneous alveolar flooding; in control regions, a sufficiently small volume of liquid is instilled that the liquid spontaneously clears from the region, leaving behind a micropunctured-but-aerated region. Fluorescent dye, at a low concentration verified not to alter surface tension, is included in the perfusate. The region is imaged by confocal microscopy over a five minute baseline period at a constant transpulmonary pressure of 5 cm $H_2O$. Five ventilation cycles are supplied to the lung, at 0.33 Hz with a positive end-expiratory pressure of 15 cm $H_2O$ and a tidal volume of 6 ml/kg body weight. The lung is then returned to a constant transpulmonary pressure of 5 cm $H_2O$ and imaged for 10 additional minutes. Alveolar liquid fluorescence at all time points is normalized by capillary fluorescence.

At baseline, alveolar liquid fluorescence (in flooded alveoli of experimental regions or in the liquid lining layer of control, aerated regions) is low and constant in all regions. Following ventilation, alveolar liquid fluorescence remains unchanged in aerated regions but continually increases with time in heterogeneously flooded regions. This result indicates that in heterogeneously flooded, but not aerated, regions, ventilation injures the alveolar-capillary barrier, permitting fluorescence to pass from the vascular perfusate to the alveolar liquid, and the injury is sustained over time. The increase above baseline in normalized alveolar liquid fluorescence at the last time point of the experiment is used as an injury score. The injury score, which indicates the rate of increase of normalized fluorescence following ventilation, correlates with surface tension of the test solution.

Method 3. Opening pressure of the immature fetal rat lung. To inflate the initially liquid-filled fetal lung for the first time, the pressure applied at the trachea must be sufficient to overcome a capillary force that is proportional to surface tension of the liquid in the lung. Thus, following instillation of a test solution in the trachea of the immature fetal rat lung, the opening pressure of the lung is indicative of the surface tension of the test solution. At embryonic day 18 or 19 (term=day 22), a fetus is delivered from a pregnant rat by uterotomy. (The normalized phospholipid content of the fetal rat lung on embryonic day 19 is 65% of that at full term.) A test solution (4-5 µl) is placed in the tip of a cannula; the cannula is inserted into the trachea and fixed in place with a suture; and a column of water, behind an air-filled cylinder that is connected to the tracheal cannula, is used to raise tracheal pressure in 10 cm $H_2O$ steps. The opening pressure that causes air to flow into the lungs is recorded, and is proportional to test solution surface tension.

Method 4. Surface tension in a liquid drop. In a 3 µl drop of liquid (normal saline+31 µM fluorescein, which does not alter surface tension, for fluid visualization+test solutes), surface tension is determined using the same method as in the adult rat lung (method #1, above). Liquid pressure in the drop is determined by servo-nulling pressure measurement; interfacial radius of curvature is determined by confocal microscopy; and air pressure is known to be atmospheric. Surface tension is calculated according to the Laplace relation and found to be 72±2 mN/m for normal saline, as expected.

Surfactant Therapy Limitations.

As noted above, surfactant therapy is successful in premature neonates but has not reduced mortality in ARDS. Even in neonates, there is room for improvement of surfactant therapy. As also noted above, the fact that high plasma protein concentrations are present in the alveolar liquid of premature neonates suggests that aeration, despite surfactant therapy, is sufficiently heterogeneous that stress concentrations are present and exacerbated by mechanical ventilation, resulting in injury to the alveolar-capillary barrier in NRDS. In translating surfactant therapy from neonates to adults while maintaining the same surfactant dosage per kg of body weight, the quantity of surfactant required becomes excessive. Use of a dilute surfactant would reduce the quantity of surfactant required. Further, there is evidence that dilute surfactant solutions distribute more homogeneously throughout the lungs than do concentrated solutions, which could be beneficial to both neonates and adults.

There are concerns about the use of animal surfactant, which include the possibility that it contains prions, which may cause brain disease. Thus attempts have been made to produce a synthetic surfactant. A synthetic surfactant could be the combination of lipids with one or more recombinant or synthetic surfactant protein. Efforts have focused on recombinant and synthetic forms of SP-C.

Surfactant protein C.

SP-C is a 4.2 kilodalton (kD), 34 amino acid peptide. It has an α-helix and an N-terminal region of undefined conformation. Two cysteine residues in the N-terminal region are palmitoylated. Various forms of recombinant SP-C and synthetic SP-C (sSP-C) have been identified and/or tested as a component of synthetic surfactant, in which the role of the recombinant or synthetic SP-C would be to promote lipid adsorption. One such form is the unpalmitoylated sSP-Css-ion lock (GIPSSPVHLKRLLIV-VVVVELIVKVIVGALLMGL (SEQ ID NO. 1)) which is disclosed in U.S. Patent Application Publication No. 2015/0125515, which is hereby incorporated herein by reference. In this peptide, serine residues are substituted for the two cysteines, to avoid cross bridge formation and aggregation in the absence of palmitoylation. Additionally, a glutamine with a negatively charged side chain and a lysine with a positively charged side chain are substituted within the α-helix region at residues 20 and 24, respectively. The oppositely charged side chains, located approximately one turn of the α-helix apart, are thought to attract one another and thus form an 'ion lock' that stabilizes the α-helix. Alternatively, also as disclosed in U.S. Patent Application Publication No. 2015/0125515, phenylananine residues may be substituted for the two cysteins, to avoid cross bridge formation and aggregation in the absence of palmitoylation. And leucines may be substituted for valines in the a-helix region. Leucines, with longer side chains than valines, help maintain a-helix integrity.

Novel Findings.

Although, to date, no synthetic surfactant has functioned as well as animal surfactant, Applicants have surprisingly found that low concentrations of surfactant, isolated SP-C or isolated sSP-C, in the presence of albumin, can lower surface tension in the lungs and thereby minimize mechanical ventilation injury to an edematous lung. Applicants have tested 1% SURVANTA® solution in conjunction with albumin and alternative negatively charged solutes; human SP-C isolated from pulmonary alveolar proteinosis patients, with albumin; sSP-Css-ion lock, with albumin; sSP-Css-ion lock-B, a variant of sSP-Css-ion lock with a biotinylated N-terminal, with albumin; and sSP-Cffleuc (GIPFF-PVHLKRLKLLLLLLLLILLLILGALLMGL (SEQ ID NO. 2)), in which phenylananine residues are substituted for the two cysteines and leucines are substituted for valines in the α-helix region, with albumin. It is believed that besides albumin, an alternative negatively charged solute, such as fibrinogen or negatively charged 70 kD dextran, would cooperate with low concentrations of isolated SP-C or sSP-C to lower surface tension in the lungs and thereby minimize mechanical ventilation injury to an edematous lung. Based on this finding, it is believed that a recombinant or synthetic SP-C, alone, could constitute a synthetic surfactant that could achieve the aforesaid goal. It is noted that, at 4.2 kD, which is smaller than the 66 kD albumin that passes from capillary to alveolus in ARDS, CPE, and NRDS, isolated SP-C could be delivered intravascularly, potentially increasing either the homogeneity of the therapy throughout the lungs or the matching of the therapy to the edematous regions that require it. The sequence listings for unpalmitoylated sSP-Css-ion lock and sSP-Cff-leuc are presented in Table 1 hereinbelow.

SUMMARY OF THE INVENTION

Methods of the present invention comprise lowering the surface tension of liquid in alveoli of the edematous lung by providing to the alveoli a surfactant-associated protein and a negatively charged solute. Dilute surfactant protein C (SP-C) interacts with albumin or another negatively charged solute, such as fibrinogen or negatively charged 70 kD dextrin, to lower surface tension. The negatively charged solute may be already present or may be added with the SP-C. SP-C could be administered via either the trachea or the vasculature. Lowering the surface tension of alveolar liquid will reduce ventilation injury of the heterogeneously flooded lung.

BRIEF DESCRIPTION OF THE DRAWINGS

For a more complete understanding of the present invention, reference is made to the following detailed description of an exemplary embodiment considered in conjunction with the accompanying drawings, in which:

FIG. 1A. Injury Score for Flooding Solutions in the Adult Rat Lung. In control, aerated regions, instilled solutions are 0-5% albumin, 5% 70 kD dextran, 10 µM NaOH or 5% 70 kD dextran plus 10 µM NaOH, all in normal saline, without (n=24) or with (n=24) 1% SURVANTA®. These solutions have surface tensions spanning the full range tested. In flooded regions, instilled liquid is normal saline with additives as specified (n=4/group). When SURVANTA® is included, its concentration is 1%. Statistics: data shown as mean±standard deviation. All groups with flooding differ from control, aerated groups (p<0.01, statistics not shown on graph); *p<0.01 vs. no SURVANTA® for same flooding liquid; #p<0.01 vs. 3% albumin plus SURVANTA® and p<0.05 vs. 5% fibrinogen plus SURVANTA®.

FIG. 1B. Surface Tension for Flooding Solutions in the Adult Rat Lung. Surface tension in alveoli flooded with normal saline plus 31 µM fluorescein and additives, as specified (n≥4/group). SURVANTA® concentration is 0.9%. Statistics: *p<0.05 vs. no SURVANTA® for same flooding liquid; #p<0.01 vs. no SURVANTA® for same flooding liquid.

FIG. 2A. Injury Score for Flooding Solutions Containing Specific Surfactant Components in the Presence of Albumin. Solutes are at about the same concentrations as present in 1% SURVANTA® solution. The SP-B and SP-C used are isolated from pulmonary alveolar proteinosis patients; the SP-C, thus, is likely a mixture of fully-, partially- and non-palmitoylated peptide. Two forms of synthetic SP-C are used. One is sSP-Cff-leuc. The other is sSP-Css-ion lock-B. Only SP-C and sSP-C lower injury score, thus lower surface tension. Base solution for all groups is normal saline with 5% albumin. Due to pre-dissolution of certain solutes, at high concentration, in non-aqueous solvents, the final DPPC solution contains 2% methanol; the final SP-B and SP-C solutions contain 1.6% chloroform and 0.8% methanol; and the final sSP-Cff-leuc solution contains 1.3% chloroform and 1.3% ethanol. The sSP-Css-ion lock-B is dissolved directly in 5% albumin solution in normal saline, without additional solvents. n=1 or 2/group. From these results it appears that albumin facilitation of dilute SURVANTA® solution is attributable to albumin-SP-C interaction.

FIG. 2B. Injury Score for Flooding Solutions Containing SP-C, With and Without Albumin and DPPC. In normal saline without albumin, SP-C fom pulmonary alveolar proteinosis patients loses its ability to lower injury score, thus lower surface tension. Inclusion of DPPC does not restore the ability of SP-C to lower injury score, thus surface tension, in the absence of albumin. Base solution for all groups is normal saline. Due to pre-dissolution of certain solutes, at high concentration, in non-aqueous solvents, the final SP-C solutions, with or without albumin, contain 1.6% chloroform and 0.8% methanol; and the final SP-C plus DPPC solution contains 1.6% chloroform and 2.8% methanol. n=1 or 2/group. From these results it appears that isolated SP-C is surface active only when facilitated by albumin.

DETAILED DESCRIPTION OF THE EXEMPLARY EMBODIMENT

Figure 1D:
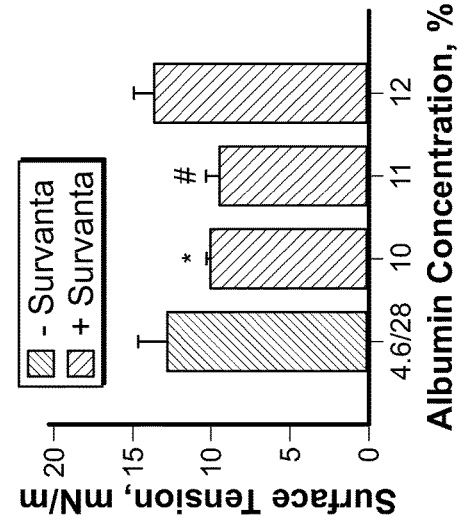
FIGS. 1C and 1D. Injury Score and Surface Tension for Flooding Solutions with Albumin Concentrations at the High End of the Effective Range in the Adult Rat Lung. Flooding solution is normal saline plus solutes as specified and, in surface tension-determination experiments, 31 µM fluorescein. SURVANTA® concentrations are 1% for ventilation injury experiments and 0.9% for surface tension determination experiments. Control groups combine data for two albumin solutions—in the absence of SURVANTA®—whose albumin concentrations bracket those of the solutions tested with SURVANTA® and between which there is no difference in injury score or surface tension. Statistics: *p<0.05 vs. control group without SURVANTA®; #p<0.01 vs. control group without SURVANTA®.
Figure 1C:
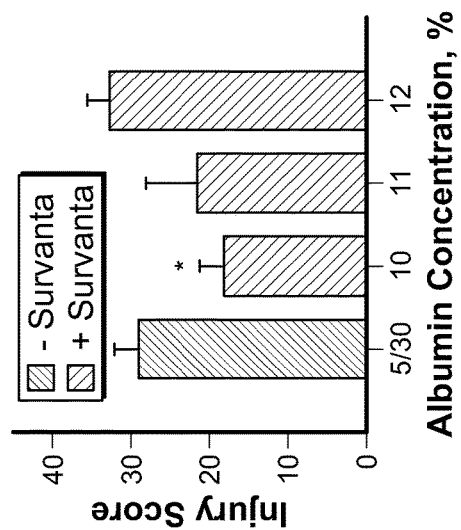
Figure 1E:
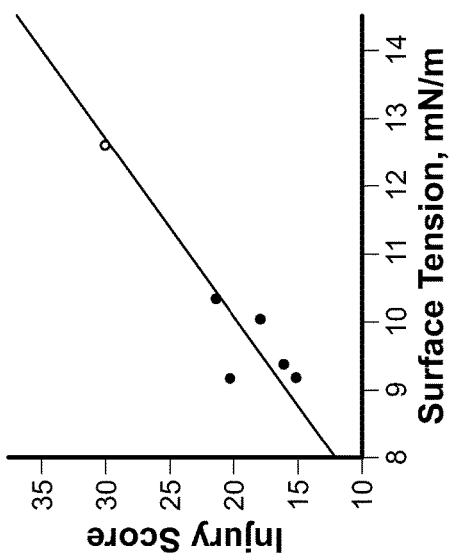
FIG. 1E. Injury Score Data Plotted vs. Surface Tension Data. Open symbol is average of data groups between which neither injury score nor surface tension differ. $R^2=0.65$.

The present invention overcomes the disadvantages and shortcomings discussed above. Four alternative methods are used to assess the surface activity of test solutions:

1. direct surface tension determination in surface alveoli of the isolated adult rat lung, which contains native lung surfactant, following alveolar instillation of a test solution;

2. degree of ventilation induced injury in a region of the isolated, perfused adult rat lung in which surface alveoli have been flooded, in a heterogeneous fashion, with a test solution;

3. initial inflation pressure of the immature fetal rat lung, which contains a reduced quantity of native surfactant compared with the adult lung, following tracheal instillation of a test solution; and 4. surface tension determination in a normal saline drop containing known quantities of additional solutes and no lipids other than any that are added to it.

The concentrations of SURVANTA discussed below are in volume percent (vol %) based on the total volume of the liquid in which the SURVANTA is dispersed.

The concentrations of SP-C, whether natural, recombinant or synthetic, discussed below are in weight/volume percent (w/v %) based on the weight (in grams) of SP-C dispersed and the volume (in tenths-of-liters) of liquid in which the SP-C is dispersed.

The concentrations of the negatively charged solute (e.g., albumin, fibrinogen or negatively charged 70 kD dextrin) discussed below are also in weight/volume percent (w/v %) based on the weight (in grams) of the negatively charged solute dispersed and the volume (in tenths-of-liters) of liquid in which the negatively charged solute is dispersed.

In practice, with human patients having an edematous lung and receiving mechanical ventilation, the volume of liquid of concern in the body (i.e., the volume of liquid in which either SP-C or a negatively charged solute, or both, is to be dispersed) is understood to be the sum of the edema liquid and blood plasma. Persons of ordinary skill in the art will be familiar with this principle and capable of calculating an estimated volume for a particular patient in need of receiving treatment, as well as calculating the therapeutically effective amount of SP-C or negatively charged solute necessary which will provide the concentrations discussed below.

The following discussion is intended to provide guidance without limiting the methods described and contemplated herein. Functional residual capacity (FRC), which is the air volume in the lung at the end of expiration, averages 2.3 liters (L) in humans. In pulmonary edema, permeability of the lung capillaries is elevated such that solutes, such as SP-C and a negatively charged solute, can pass between the alveolar edema liquid and the blood plasma. Therefore, the plasma volume, which averages 3 L, should be included in the calculation of the volume of concern. As recognized by persons of ordinary skill in the art, a particular human patient's weight and hematocrit values will aid in estimating the plasma volume.

Assuming that, in a human patient with pulmonary edema, somewhere between 5 and 80% of FRC were flooded with liquid, then the total volume of edema liquid would be 0.12-1.8 L (based on the average 2.3 L mentioned above) and the total volume of edema liquid plus blood plasma would be 3.1-4.8 L. This would be the total volume of the liquid of concern upon which to base further calculations of the range of amounts of SP-C and the negatively charged solute that would be required to be therapeutically effective at providing the concentrations discussed below. More particularly, therapeutically effective amounts of SP-C and the negatively charged solute are those amounts that, directly or indirectly, minimize mechanical ventilation injury to an edematous lung by reducing the surface tension of alveolar liquid so that stress concentrations and alveolar flooding heterogeneity are reduced. As surprisingly discovered and described herein, therapeutically effective amounts of SP-C and the negatively charged solute are those amounts that provide the concentrations of these substances in the volume of liquid of concern as discussed hereinbelow because those concentrations of SP-C and the negatively charged solute reduce the surface tension of alveolar liquid.

From the results of testing based on the four methods described in the background above, it has been found that:

1. A dilute solution of 1 vol % SURVANTA® in normal saline is not surface active, but that solutions of 1-5 vol % SURVANTA® are surface active when facilitated by 5% albumin solution. Further, based on the test results reported in FIG. 2, it is the SP-C in SURVANTA® that interacts with albumin; solutions of various forms of natural and synthetic SP-C at concentrations comparable to that in 1 vol % SURVANTA® are surface active in the adult or fetal rat lung, but only when facilitated by albumin solution. A solution of SP-C plus albumin tends to lose its surface activity in vitro in the absence of lipids, however, suggesting the SP-C and albumin, together, may reduce surface tension by promoting the adsorption of surfactant lipids.

Dilute surfactant solution or SP-C solution, where the SP-C may be natural, recombinant or synthetic, could be administered intratracheally in some embodiments. With sufficient albumin present in the alveolar liquid, dilute surfactant or SP-C solution could simply be administered in buffer (normal saline, Ringer's solution, physiologic saline solution, or equivalent). Without sufficient albumin present, a facilitating negatively charged solute (e.g., albumin, fibrinogen, negatively charged dextran or alternative negatively charged solute) could be added to the administered composition. The surfactant in the dilute surfactant solution may be SURVANTA® or another surfactant isolated from an animal that comprises SP-C. Suitable recombinant or synthetic SP-C are reasonably believed to include any of those identified in U.S. Patent Application Publication No. 2015/0125515, which has already been mentioned and incorporated herein by reference above.

Dilute surfactant solution or SP-C solution, where the SP-C may be natural, recombinant or synthetic, could alternatively be administered intravascularly, in the absence or presence of exogenous albumin or of an alternative negatively charged facilitating solute. Again, the surfactant in the dilute surfactant solution may be SURVANTA® or another surfactant isolated from an animal that comprises SP-C.

2. Albumin or alternative negatively charged solutes (e.g., fibrinogen, negatively charged 70 kD dextran) facilitate the surface activity of dilute SURVANTA® solution containing SP-C. The surface activity of the dilute SURVANTA® solution in normal saline was assessed by three of the four surface tension determination methods discussed in the background above.

Albumin concentrations of 3-11 w/v % facilitate the surface activity of 1 vol % SURVANTA® solution in the adult rat lung. Alternatively, 5 w/v % fibrinogen or 5 w/v % negatively charged 70 kD dextran (negative charge imparted by inclusion of 10 μM NaOH) also facilitate 1 vol % SURVANTA®. In contrast, 5 w/v % neutral 70 kD dextran does not facilitate 1 vol % SURVANTA®. Thus osmotic pressure is not sufficient to facilitate 1 vol % SURVANTA®; a negatively charged solute is required. Control experiments have shown 10 μM NaOH alone, without dextran, has no effect on surface tension or lung injury in the absence or presence of SURVANTA® (see FIGS. 1A and B).

Figure 4:
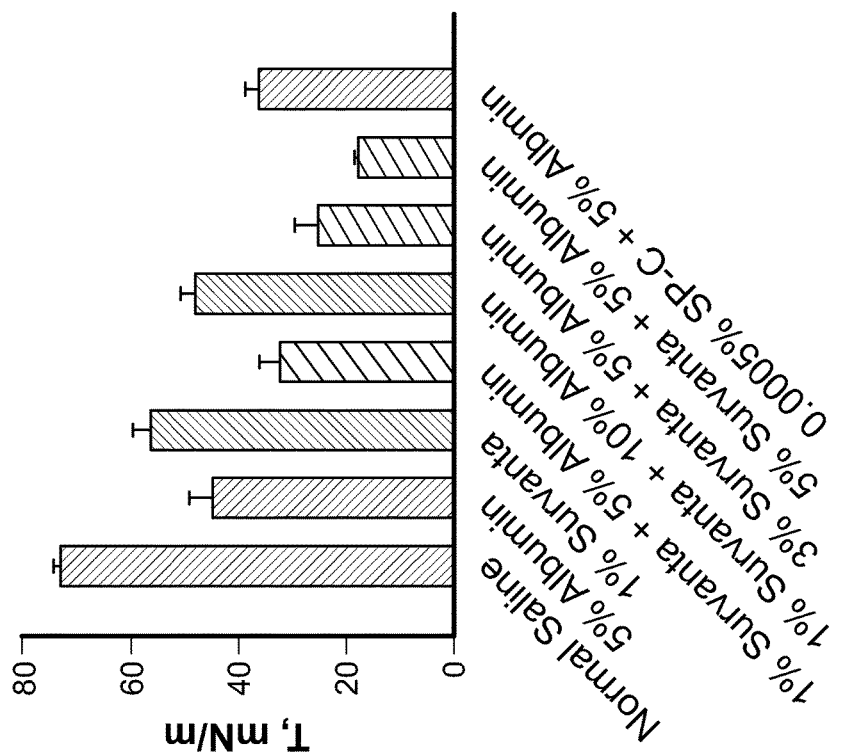
FIG. 4. Surface Tension for Solutions In Vitro. Surface tension of normal saline drops (3 µl) containing 31 µM fluorescein and additional solutes as specified. The SP-C solution additionally contains 1.6% chloroform and 0.8% methanol. The fourth, sixth and seventh bars show that, in the presence of 5% albumin, surface tension decreases with increasing SURVANTA® concentration. The third, fourth and fifth bars demonstrate that there is an optimal albumin concentration of ~5% for the facilitation of 1% SURVANTA®. n=2 or 3/group.
Figure 3:
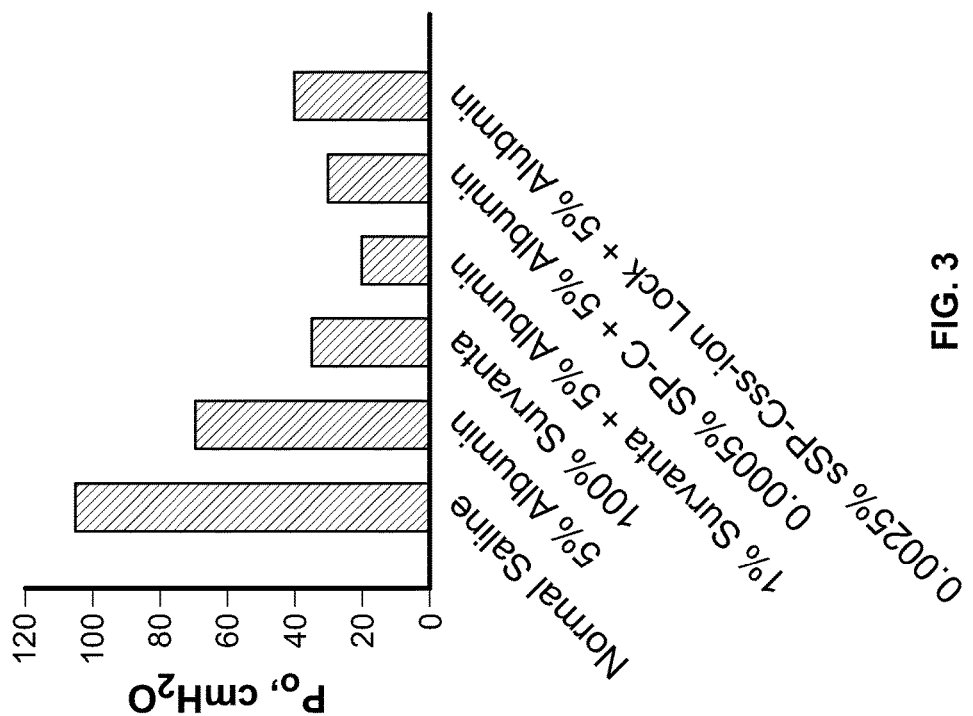
FIG. 3. Opening Pressure for Tracheal Instillation Solutions in the Immature Fetal Rat Lung. Solution (4-5 µl), with solutes as specified, is instilled in the trachea of the fluid-filled immature (embryonic day 18 or 19) fetal rat lung. The pressure required to inflate the fetal rat lung for the first time is proportional to surface tension. Base solution is normal saline excepting that base solution is Ringer's solution for 1% SURVANTA® plus 5% albumin. The solution of 0.0005% SP-C plus 5% albumin additionally includes 1.6% chloroform and 0.8% methanol. The sSP-Css-ion lock used is not biotinylated and is dissolved directly in normal saline without additional solvents. n=1 or 2/group.

In vitro, albumin is likewise required to facilitate the surface activity of SURVANTA®. However, the albumin concentration range that facilitates 1 vol % SURVANTA® does not extend to 10 vol %. Further, as shown by the data in FIG. 4, dose-response experiments demonstrate that, in conjunction with 5 w/v % albumin, 5 vol % SURVANTA® lowers surface tension more than 1 vol % SURVANTA®.

3. Surfactant protein C is the SURVANTA® component that interacts with albumin to lower surface tension. SURVANTA® contains 2.5% total phospholipids, which includes 1.1-1.6% DPPC, and <0.1% of SP-B and SP-C combined, with a concentration of SP-C that is up to 15 times that of SP-B. Thus 1% SURVANTA® solution contains 0.025% total phospholipids, ~0.01% DPPC, <0.001% SP-C and <<0.001% SP-B. The surface activity of solutions containing DPPC, SP-B and SP-C, in concentrations comparable to those in 1 vol % SURVANTA® solution, was assessed by ventilation injury assay (method #2). In conjunction with 5 w/v % albumin solution, only solutions with SP-C or sSP-C lower injury score, thus surface tension. Surfactant protein C alone, without albumin, is not surface active. Neither is the combination of SP-C and DPPC, in the absence of albumin, surface active.

4. The combination of SP-C and albumin lowers surface tension in the presence of at least a low concentration of surfactant lipids. The combination of SP-C, or sSP-C, and albumin lowers surface tension in the adult rat lung with normal levels of native surfactant and in the immature fetal rat lung with reduced surfactant levels. The combination of SP-C and albumin is likewise surface active in in vitro tests of dilute 1-5 vol % SURVANTA® containing only 0.03-0.13 w/v % total phospholipids (compared with 2.5 w/v % in undiluted SURVANTA®). Thus the combination of SP-C and albumin is surface active in the presence of low lipid concentrations. However, the combination of SP-C and albumin in the absence of any lipids demonstrates only low surface activity in vitro. The combination of SP-C and albumin appears to be highly effective at promoting lipid adsorption, but to require the presence of at least a low lipid level for surface activity.

By extension of the above findings, it is expected that a concentration of from greater than about 2 w/v % to less than about 12 w/v % of a negatively charged solute (e.g., albumin, fibrinogen, and negatively charged 70 kD dextran), will facilitate the surface activity of a concentration of at least 0.01 vol % SURVANTA® or other surfactants isolated from animals; or of from about 0.000001 w/v % to about 1 w/v % SP-C, whether natural, recombinant or synthetic, in the presence of at least low levels of surfactant lipids, the relative proportions of which might be the same as or different from that in natural lung surfactant. This effect is reasonably expected regardless of whether the negatively charged solute is included in the delivered composition or already present, for example, in edema liquid or blood plasma. The recombinant or synthetic SP-C peptides that could be used include sSP-Css ion lock; sSP-Css ion lock-B; sSP-Css-ion lock with biotin tags(s) in alternative locations; sSP-Cff-leuc; biotinylated sSP-Cff-leuc; or alternative variations of natural human or animal SP-C.

In some embodiments, the therapeutically effective concentration of SP-C (natural, recombinant or synthetic) in the liquid of concern may be, for example without limitation, from about 0.00001 w/v % to about 1 w/v %, or from about 0.0005 w/v % to about 1 w/v %, or from about 0.0001 w/v % to about 1 w/v %, or from about 0.005 to about 1 w/v %, or from about 0.0025 w/v % to about 1 w/v %, or from about 0.00001 w/v % to about 0.05 w/v %, or from about 0.0005 w/v % to about 0.05 w/v %, or from about 0.0001 w/v % to about 0.05 w/v %, or from about 0.005 to about 0.05 w/v %, or from about 0.0025 w/v % to about 0.05 w/v %, 0.00001 w/v % to about 0.01 w/v %, or from about 0.0005 w/v % to about 0.01 w/v %, or from about 0.0001 w/v % to about 0.01 w/v %, or from about 0.005 to about 0.01 w/v %, or from about 0.0025 w/v % to about 0.01 w/v %, or from about 0.00001 w/v % to about 0.1 w/v %, or from about 0.0005 w/v % to about 0.1 w/v %, or from about 0.0001 w/v % to about 0.1 w/v %, or from about 0.005 to about 0.1 w/v %, or from about 0.0025 w/v % to about 0.1 w/v %, In some embodiments, the therapeutically effective concentration of the negatively charged solute in the liquid of concern may be, for example without limitation, from about 2.1 w/v % to about 11.9 w/v %, or from about 2.5 w/v % to about 11.9 w/v %, or from about 3 w/v % to about 11.9 w/v %, or from about 4 or from about 3 w/v % to about 11.9 w/v %, or from about 5 w/v % to about 11.9 w/v %, or from about 6 w/v % to about 11.9 w/v %, or from about 2.1 w/v % to about 11.5 w/v %, or from about 2.1 w/v % to about w/v %, or from about 2.1 w/v % to about 10 w/v %, or from about 2.1 w/v % to about 9 w/v %, or from about 2.5 w/v % to about 11.5 w/v %.

TABLE 1

SEQUENCE LISTING

```
<110> Stevens Inst. of Tech.
Perlman, Carrie

<120> DILUTE SURFACTANT OR ISOLATED SURFACTANT
PROTEIN SOLUTION FOR THE REDUCTION OF SURFACE
TENSION IN THE LUNG

<130> 101995.043101

<160> 2

<170> PatentIn version 3.5

<210> 1
<211> 34
<212> PRT
<213> Artificial Sequence

<220>
<223> sSP-Css-ion lock

<400> 1
Gly Ile Pro Ser Ser Pro Val His Leu Lys Arg
1           5           10            15

Leu Leu Ile Val Val Val Val Val Glu Leu Ile
                            20            25

Val Lys Val Ile Val Gly Ala Leu Leu Met Gly
            30

Leu

<210> 2
<211> 34
<212> PRT
<213> Artificial Sequence

<220>
<223> sSP-Cff-leuc

<400> 2
Gly Ile Pro Phe Phe Pro Val His Leu Lys Arg
1           5           10          15

Leu Lys Leu Leu Leu Leu Leu Leu Leu Leu Ile
                          20            25

Leu Leu Leu Ile Leu Gly Ala Leu Leu Met Gly
         30

Leu
```

SEQUENCE LISTING

```
<160> NUMBER OF SEQ ID NOS: 2

<210> SEQ ID NO 1
<211> LENGTH: 34
<212> TYPE: PRT
<213> ORGANISM: Artificial Sequence
<220> FEATURE:
<223> OTHER INFORMATION: sSP-Css-ion lock
```

-continued

```
<400> SEQUENCE: 1

Gly Ile Pro Ser Ser Pro Val His Leu Lys Arg Leu Leu Ile Val Val
1               5                   10                  15

Val Val Val Glu Leu Ile Val Lys Val Ile Val Gly Ala Leu Leu Met
            20                  25                  30

Gly Leu

<210> SEQ ID NO 2
<211> LENGTH: 34
<212> TYPE: PRT
<213> ORGANISM: Artificial Sequence
<220> FEATURE:
<223> OTHER INFORMATION: sSP-Cff-leuc

<400> SEQUENCE: 2

Gly Ile Pro Phe Phe Pro Val His Leu Lys Arg Leu Lys Leu Leu Leu
1               5                   10                  15

Leu Leu Leu Leu Leu Ile Leu Leu Leu Ile Leu Gly Ala Leu Leu Met
            20                  25                  30

Gly Leu
```

The invention claimed is:

1. A method of reducing ventilation injury to a patient whose lung has regions with heterogeneous alveolar flooding by alveolar liquid, said method comprising the step of (i) delivering to the patient a solution comprising a predetermined amount of a surfactant protein C and a negatively charged solute, wherein said negatively charged solute is present in the alveolar liquid in a concentration which is in a range of from greater than 2 weight/volume percent to less than 12 weight/volume percent after the performance of step (i) and wherein said predetermined amount of said surfactant protein C is selected to provide a concentration of said surfactant protein C in the alveolar liquid in a range of from 0.000001 weight/volume percent to 1 weight/volume percent, said weight/volume percent of said surfactant protein C and said negatively charged solute being based on the total volume of the alveolar liquid after the performance of step (i).

2. The method of claim 1, wherein said surfactant protein C is natural, recombinant, or synthetic.

3. The method of claim 2, wherein said surfactant protein C is synthetic and selected from sSP-Css-ion lock, sSP-Css-ion lock-B, sSP-Cff-leuc, and combinations thereof.

4. The method of claim 1, wherein said concentration of said surfactant protein C in the alveolar liquid is in a range of from 0.0005 weight/volume percent to 1 weight/volume percent.

5. The method of claim 1, wherein said concentration of said surfactant protein C in the alveolar liquid is in a range of from 0.00001 weight/volume percent to 1 weight/volume percent.

6. The method of claim 1, wherein said concentration of said surfactant protein C in the alveolar liquid is in a range of from 0.00001 weight/volume percent to 0.1 weight/volume percent.

7. The method of claim 1, wherein said negatively charged solute is present in the alveolar liquid in a concentration which is in a range of from 2.1 weight/volume percent to 11 weight/volume percent.

8. The method of claim 1, wherein said surfactant protein C is derived from an animal.

9. The method of claim 1, wherein said solution comprises a surfactant containing said surfactant protein C.

10. The method of claim 1, wherein said solution further comprises lipids.

11. The method of claim 1, wherein step (i) is performed such that the lowered surface tension of the alveolar liquid lessens ventilation-induced over-distension injury of intervening septa located between aerated and flooded alveoli.

12. The method of claim 1, wherein step (i) comprises the step of administering said solution comprising said surfactant protein C to a trachea or bronchus of the patient having the lung.

13. The method of claim 1, wherein step (i) comprises the step of administering said solution comprising said surfactant protein C by injecting said solution into a circulatory system of the patient having the lung.

14. The method of claim 1, wherein the concentration of said surfactant protein C in the alveolar liquid is in a range of from 0.00001 weight/volume % to 0.1 weight/volume percent.

15. The method of claim 1, wherein the concentration of said surfactant protein C in the alveolar liquid is in a range of from 0.0005 weight/volume percent to 0.05 weight/volume percent.

16. The method of claim 1, wherein the concentration of said surfactant protein C in the alveolar liquid is in a range of from 0.00001 weight/volume percent to 0.05 weight/volume percent.

17. The method of claim 1, wherein the concentration of said surfactant protein C in the alveolar liquid is in a range of from 0.0001 weight/volume percent to 0.05 weight/volume percent.

18. The method of claim 1, wherein the concentration of said surfactant protein C in the alveolar liquid is in a range of from 0.005 weight/volume percent to 0.05 weight/volume percent.

19. The method of claim 1, wherein the concentration of said surfactant protein C in the alveolar liquid is in a range of from 0.0025 weight/volume percent to 0.05 weight/volume percent.

20. The method of claim 1, wherein the concentration of said surfactant protein C in the alveolar liquid is in a range of from 0.00001 weight/volume percent to 0.01 weight/volume percent.

21. The method of claim 1, wherein the concentration of said surfactant protein C in the alveolar liquid is in a range of from 0.0005 weight/volume percent to 0.01 weight/volume percent.

22. The method of claim 1, wherein the concentration of said surfactant protein C in the alveolar liquid is in a range of from 0.0001 weight/volume percent to 0.01 weight/volume percent.

23. The method of claim 1, wherein the concentration of said surfactant protein C in the alveolar liquid is in a range of from 0.005 weight/volume percent to 0.01 weight/volume percent.

24. The method of claim 1, wherein the concentration of said surfactant protein C in the alveolar liquid is in a range of from 0.0025 weight/volume percent to 0.01 weight/volume percent.

25. The method of claim 1, wherein the concentration of said surfactant protein C in the alveolar liquid is in a range of from 0.0005 weight/volume percent to 0.1 weight/volume percent.

26. The method of claim 1, wherein the concentration of said surfactant protein C in the alveolar liquid is in a range of from 0.0001 weight/volume percent to 0.1 weight/volume percent.

27. The method of claim 1, wherein the concentration of said surfactant protein C in the alveolar liquid is in a range of from 0.005 weight/volume percent to 0.1 weight/volume percent.

28. The method of claim 1, wherein the concentration of said surfactant protein C in the alveolar liquid is in a range of from 0.0025 weight/volume percent to 0.1 weight/volume percent.

* * * * *

UNITED STATES PATENT AND TRADEMARK OFFICE
CERTIFICATE OF CORRECTION

PATENT NO. : 10,391,151 B2
APPLICATION NO. : 15/194096
DATED : August 27, 2019
INVENTOR(S) : Carrie E. Perlman Page 1 of 1

It is certified that error appears in the above-identified patent and that said Letters Patent is hereby corrected as shown below:

In the Specification

Column 1, Line 17, replace the paragraph below the section heading "Statement Regarding Federally Sponsored Research" with the following paragraph:
-- This invention was made with government support under Grant Number HL113577 awarded by The National Institutes of Health. The government has certain rights in the invention. --

Signed and Sealed this
Fourth Day of May, 2021

Drew Hirshfeld
*Performing the Functions and Duties of the
Under Secretary of Commerce for Intellectual Property and
Director of the United States Patent and Trademark Office*